United States Patent [19]

Fried et al.

[11] 4,108,870

[45] Aug. 22, 1978

[54] STEREOCONTROLLED SYNTHESIS OF α-MULTISTRIATIN

[75] Inventors: Josef Fried; William J. Elliott, both of Chicago, Ill.

[73] Assignee: University of Chicago, Chicago, Ill.

[21] Appl. No.: 803,734

[22] Filed: Jun. 6, 1977

[51] Int. Cl.² ........................................... C07D 317/08
[52] U.S. Cl. .............................. 260/340.9 R; 260/338
[58] Field of Search ................................. 260/340.9 R

[56] References Cited

U.S. PATENT DOCUMENTS

| | | | |
|---|---|---|---|
| 2,511,891 | 6/1950 | Whetstone | 260/340.9 |
| 3,755,365 | 8/1973 | Frentiman et al. | 260/340.9 |

OTHER PUBLICATIONS

Gore et al., J. Org. Chem., 40, No. 12, 1975, pp. 1705–1708.

*Primary Examiner*—Ethel G. Love
*Attorney, Agent, or Firm*—Mathew L. Kalinowski

[57] ABSTRACT

A practical stereocontrolled synthesis of a mixture containing a major amount of α-multistriatin and a minor amount of γ-multistriatin in an overall yield of about 73% from cis-2-butene-1,4-diol is provided. α-Multistriatin is one of the three essential components of the aggregation pheromone of the European elm bark beetle.

7 Claims, No Drawings

STEREOCONTROLLED SYNTHESIS OF α-MULTISTRIATIN

The invention described herein was made in the course of work under grants from the National Institute of Health and the National Science Foundation.

This invention relates to the stereocontrolled synthesis of α- and γ-(2,4-dimethyl-5-ethyl-6,8-dioxabicyclo[3.2.1]octane). The two isomers, hereinafter referred to as α- and γ-multistriatin, are represented by the following structural formulas:

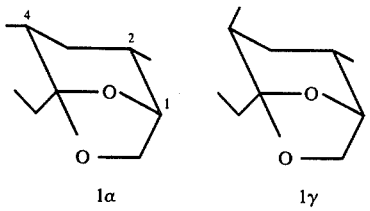

This invention also relates to the resolution of α- and γ-multistriatin into their optically active forms.

The aggregation pheromone for the European elm bark beetle, *Scolytus multistriatus* (Marsham), which is the principal vector of Dutch elm disease in the United States, has been recently characterized as a three-component mixture (Silverstein et al., *J. Chem. Ecol.*, 1, 115[1975]). One of the active compounds has been named α-multistriatin and has been assigned the structure 1α (Silverstein et al., *J. Org. Chem.*, 40, 1705[1975]). The other two components are (−)-4-methyl-3-heptanol and (−)-α-cubebene. The first two components are beetle-produced pheromones, the third a host-produced synergist. The use of α-multistriatin alone or in admixture with (−)-4-methyl-3-heptanol or (−)-α-cubebene or both as attractants for the control of the elm bark beetle makes α-multistriatin a highly desirable target for chemical synthesis.

Of the two previous syntheses reported by Silverstein et al. in the above-cited references the first, a non-stereospecific approach, served to elucidate and confirm the structure of the molecule; the second was designed to prove its stereochemistry. Although stereocontrolled, it proceeded in less than 2.5% overall yield.

In contrast, the synthesis of this invention yields multistriatin as an 85:15 mixture of alpha- and gamma-isomers in an overall yield of 73% from commercially available cis-2-butene-1,4-diol. In the first step, the butene diol is converted to the required acetonide alcohol 2 according to the following reaction scheme:

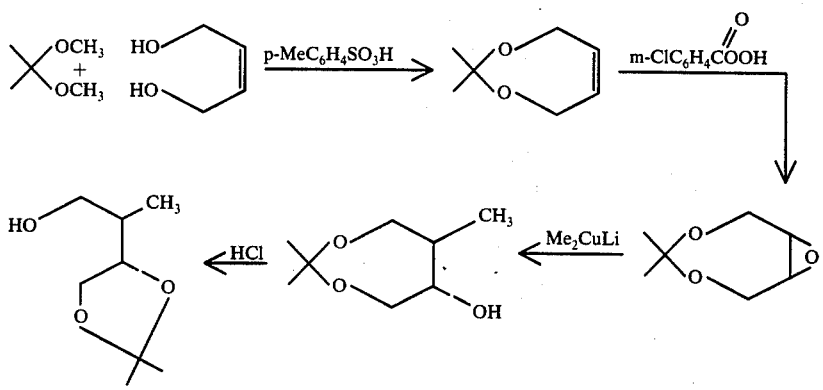

The reactions involved in the preparation of 2 are described in detail by Elliott et al., *J. Org. Chem.*, 41, 2469 (1976) which citation is incorporated herein by reference.

The alcohol 2 is converted to the iodopropane 4 in the following reaction steps:

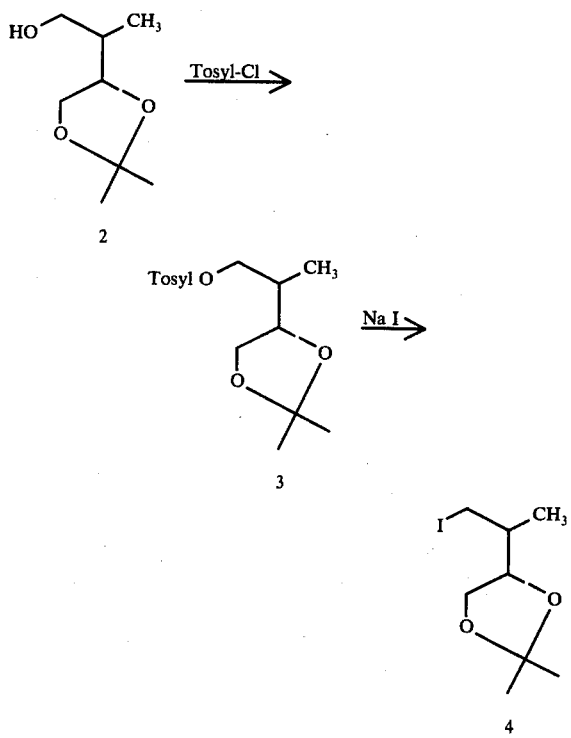

The iodopropane possesses the correct threo configuration at C-1 and C-2 of both α- and γ-multistriatin.

The next step in the overall synthesis is the alkylation of 3-pentanone with the iodopropane 4 to form compound 5 as follows:

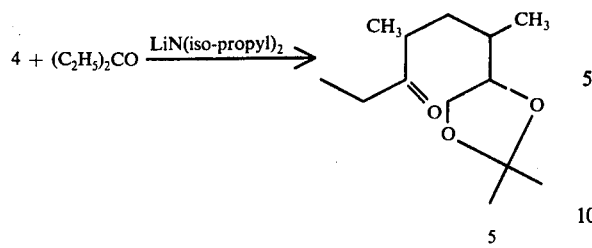

The alkylation of 3-pentanone with the iodopropane may be accomplished either via the pyrrolidine enamine method of Stork et al., *J. Am. Chem. Soc.*, 85, 207(1963), or via the magnesium salt of t-butylimine method of Stork et al., *J. Am. Chem. Soc.*, 85, 2178(1963). According to the novel method of this invention, however, the alkylation is accomplished by reaction of the enolate of 3-pentanone with the iodopropane 4 in tetrahydrofuran in presence of hexamethylphosphoramide (HMPA) at room temperature. This method affords approximately 95) % of the mixture of diastereomeric ketones.

In a final step, the acetonide grouping of compound 5 is removed and the molecule is cyclized by treatment with 1N HCl in 2:1 acetonitrile-$H_2O$ for 18 hours, which provides multistriatin in quantitative yield in an 85:15 ratio of α- and γ-isomers. That no detectable amounts of beta or delta isomers were formed in this sequence of reactions attests to the stereospecificity of this synthesis.

It is a further aspect of this invention to prepare the final product 1α in optically active form rather than as the racemate. This causes the pheromone activity to be increased by a factor of two, since only the (−)-enantiomer of 1α is active and the (+) isomer is inactive.

In order to obtain the optically active 1α and 1γ(85:15) mixture the intermediate 6 is resolved into the optical antipodes as follows:

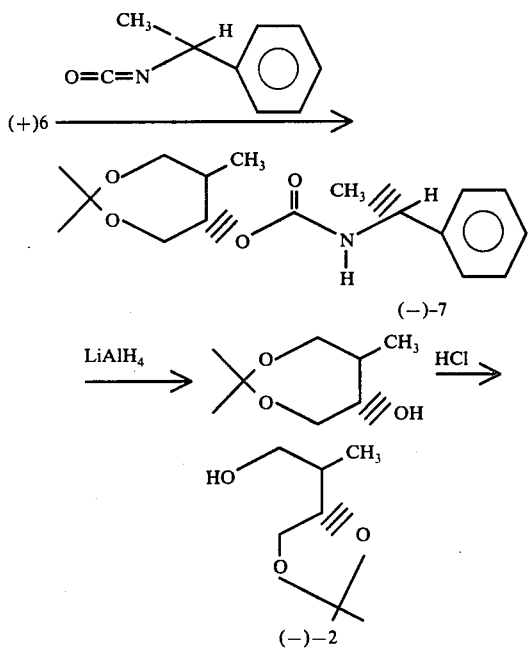

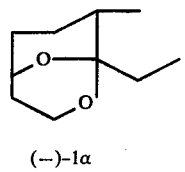

(−)-1α

(±)-6 is reacted with (+)-(R)-α-phenethylisocyanate which results in conversion to two diastereomeric urethanes which can be separated by crystallization from hexane/toluene (10:1). The resulting material ((−)-7), which melts at 103° and has an $[\alpha]_D^{23}$ −1.9° is then reduced with lithium aluminum hydride in tetrahydrofuran to furnish the parent alcohol $[\alpha]_D^{23}$ −43.5° ((−)-6).

(−)-6 is then converted into (−)-2 with hydrochloric acid. Using (−)-2 as the starting material in place of (±)-2 in the sequence described on page 4 yields the tosylate (−)-3, the iodide (−)-4, the alkylation product (+)-5 and finally the finished product mixture of (−)-1α and (−)-1γ in an 85:15 ratio.

PREFERRED EMBODIMENTS OF THE INVENTION

The invention may be more readily understood by reference to the following procedures and working examples.

Ir spectra were recorded on a Perkin-E' ler Model 137 spectrophotometer. Liquid samples were run as a thin film between NaCl plates. NMR spectra were determined as solutions in $CDCl_3$ with $Me_4Si$ as an int⁓rnal standard. Chemical shifts are reported in δ, coupling constants (J) are r⁓ported in hertz; the abbreviations s, d, t, q, and m signify singlet, doublet, triplet, quartet, and multiplet, respectively. $^1H$ NMR spectra were recorded on a Bruker HX-270 (270 MHz) spectrometer in the pulsed Fourier transform mode. $^{13}C$ NMR spectra were recorded on a Bruker HX-90E spectrometer operating at 22.63 MHz in the pulsed Fourier transform mode. Free induction decay data were accumulated and processed with a Nicolet 1089 computer. Low-resolution mass spectra were determined using a Finnigan 1015 quadrupole mass spectrometer equipped with VPC, gas and solid probe inlets; the data were recorded and processed by a Systems Industries Computer Interface System/150, and plotted as bar graphs. High-resolution mass spectra were determined on an AEI MS-9 spectrometer fitted with a PDP-8/I computer system for data analysis. High-pressure liquid chromatography was carried out using Quantum Industries TLC grade silica gel (no binder) in glass columns. Separation of multistriatin isomers was carried out using an F and M Model 400 gas chromatograph with a 6 ft. × 0.125 in. glass column containing 1.5% Carbowax 20M on 100/120 Chromosorb G at 80° C. All optical rotations were taken in $CHCl_3$ at about c=1 unless otherwise noted.

EXAMPLE 1

(2'RS, 4SR)-2'-(2,2-Dimethyl-1,3-dioxacyclopent-4-yl)-1'-propyl Tosylate 4.

To a solution of 503.5 mg (3.14 mmol) of the acetonide alcohol 2 in 8 ml of pyridine, cooled to 0° C, was added 1.1996 g (6.3 mmol) of tosyl chloride and the solution stirred at 0° C for 2 h and then at room temperature for 3 h. Cold H$_2$O (50 ml) was added and the liquid extracted with 4 × 35 ml of ether. The ether layers were combined, washed with 2 × 35 ml of 5% HCl and 3 × 50 ml of saturated NaHCO$_3$, and dried over MgSO$_4$. Evaporation of the ether gave 978.2 mg (99%) of an oil that was 99% pure by NMR. This material was thermally unstable when kept neat at room temperature, and was therefore used immediately in the next reaction. $^1$H NMR δ 7.60, AA'BB', 4 H (aromatic protons); 4.03, m, 1H (CHO); 3.95, d, J=6.5 Hz, 2 H(CH$_2$OTs); 3.91, m, 1 H(OCHCH$_2$O); 3.60, t, J=6.7 Hz, 1 H(OCHCH$_2$O); 2.45, s, 3 H(CH$_3$Ar—); 1.98, septet, J=6.5 Hz, 1 H(CH$_3$CH); 1.32, s, 3 H(acetonide CH$_3$); 1.28, s, 3 H(acetonide CH$_3$); 0.95, d, J=6.5 Hz, 3 H(CH$_3$CH). $^{13}$C NMR δ 144.8, s(para C); 132.9, s(sulfur-bearing C); 129.9, d(meta C's); 127.9, d,(ortho C's); 108.8, s(C-2 of dioxolane); 76.2, d(C-4 of dioxolane); 72.1, t(C-1 of propyl); 67.1, t(C-5 of dioxolane); 36.0, d(C-2 of propyl); 26.2, q(methyl of dioxolane cis to alkyl chain); 25.2, q(methyl of dioxolane trans to alkyl chain); 21.6, q(tosyl methyl); 11.8, q(C-3 of propyl). Ir 1361, 1186 (SO$_2$OR); 971; 820 cm$^{-1}$ (para-disubstituted benzene). Mass spectrum (10% cutoff) m/e 299, 1.9% (M$^+$ — CH$_3$); 172, 65% (TsOH$^+$); 155, 10% (Ts$^+$); 107, 44%; 91, 100% (PhCH$_2$$^+$); 65, 56%; 57, 55% (CH$_3$COCH$_2$$^+$); 43, 14% (CH$_3$C≡O$^+$).

When (2'R, 4S)-2'-(2,2-dimethyl-1,3-dioxacyclopent-4-yl)-1'-propanol, (−)-2, is used in place of the racemate in Example 1 there is obtained (2'R, 4S)-2'-(2,2-dimethyl-1,3-dioxacyclopent-4-yl)-1'-propyl tosylate, (−)-3; [α]$_D$ −8°.

EXAMPLE 2

(2'RS, 4RS)-2'-(2,2-Dimethyl-1,3-dioxacyclopent-4-yl)-1'-iodopropane 4.

A solution of 394.7 mg of the tosylate 3 is 5 ml of distilled acetone and 502.3 mg of NaI was stirred for 18 h, and the resulting precipitate filtered. An additional 201.3 mg of NaI was added, and the mixture stirred for 30 more h, after which it was filtered, and the filtrate poured into 50 ml of H$_2$O and extracted with 4 × 50 ml of ether. The combined layers were washed with 50 ml of 10% Na$_2$SO$_3$ and dried over MgSO$_4$, and the ether was evaporated. The resulting pale yellow oil was distilled at 20 mTorr at 55° C in a microstill to give 340 mg (99%) of a clear oil. The oil decomposed to a black tar when allowed to remain at room temperature in air for 24 h, or upon heating above 60° C. It could be stored for at least 6 months in hexane over copper wire. $^1$H NMR δ 4.08, m, 1 H(CHOCH$_2$); 4.06, m, 1 H(CH$_2$O); 3.63, m, 1 H(CH$_2$O); 3.26, d of d, J=6, 12.4 Hz, 1 H(CH$_2$I); 3.03, d of d, J=7.2, 12.4 Hz, 1 H(CH$_2$I); 1.76, m, 1 H(CH$_3$CH); 1.41, s, 3 H(acetonide CH$_3$); 1.34, s, 3 H(acetonide CH$_3$); 1.09, d, J=6 Hz, 3 H(CH$_3$CH). $^{13}$C NMR δ 108.6, s(C-2 of dioxolane); 78.3, d(C-4 of dioxolane); 66.8, t(C-5 of dioxolane); 38.3, d(C-2 of propane); 26.3, q(methyl of dioxolane cis to alkyl group); 25.2, q(methyl of dioxolane trans to alkyl group); 16.2, q(C-3 of propane); 10.7, t(C-1 of propane). Ir 2950 (CH); 1490, 1480 (methyls); 1205; 1065 (C—O—C); 862 cm$^{-1}$. Mass spectrum (20% cutoff) m/e 270, 0.02% (M$^+$); 255, 38% (M$^+$ — CH$_3$); 195, 20%; 101, 40% (2,2-dimethyl-1,3-dioxacyclopent-4-yl ion); 43, 100%, (CH$_3$C≡O$^+$). High-resolution MS, calcd for C$_8$H$_{15}$O$_2$(M$^+$ — I), 143.1072; found, 143.1077, 143.1065.

If in place of the racemic tosylate 3 there is used (−)-3 there is obtained (2'S, 4S)-2'-(2,2-dimethyl-1,3-dioxacyclopent-4-yl-1'-iodopropane, (−)-4; [α]$_D$ −0.5°.

EXAMPLE 3

(2'RS, 4SR)-2'-(2,2-Dimethyl-1,3-dioxacyclopent-4-yl)-4'-ξ-methylhept-5'-one 5.

To a dry 25-ml flask were added under N$_2$ 0.7 ml (5.0 mmol) of freshly distilled diisopropylamine, 3 ml of dry THF, and a stirring bar. After cooling to −78° C, 3.75 ml of a 1.3 M n-BuLi solution was added, and the contents of the flask stirred for 30 min. Then 0.52 ml (4.94 mmol) of freshly distilled diethyl ketone in 5 ml of THF was added and the solution stirred for 0.5 h while warming to −40° C. A solution of 270 mg (1 mmol) of the iodide 4 in 5 ml of THF and 1.79 g of HMPA was added and the solution stirred for 2 days at room temperature. The yellow mixture was then poured into 30 ml of saturated NaCl, and the H$_2$O layer extracted with 4 × 20 ml of ether. The ether layers were combined, washed with 2 × 50 ml of 10% HCl and 50 ml of saturated NaHCO$_3$, and dried over MgSO$_4$. The ether was evaporated and the residue of 249 mg was distilled in a microstill to give 227.4 mg of the desired ketone 5 (95%). This material was a mixture of two diastereomers as shown by NMR, which could not be separated by GLC. $^1$H NMR δ 4.01, complex q, 1 H(CHO); 3.87, m, 1 H(CH$_2$O); 3.61, m, 1 H(CH$_2$O); 2.73, m(C-4'H); 2.65, m, 1 H(C-2'H); 2.49, q, 2 H(C-6'H$_2$); 1.70, m, 2 H(C-3'H$_2$); 1.34, s, 3 H(acetonide CH$_3$); 1.26, s, 3 H(acetonide CH$_3$); 1.09, d, J=7 Hz, 3 H(C-4'CH$_3$); 1.05, t, J=7 Hz, 3 H(C-7'); 0.94, d, J=7 Hz, 3 H(C-1'). The resonance at δ 0.94 is split into two doublets in a 60:40 ratio separated by less than 2 Hz at 270 MHz; the resonance at σ 1.34 is also split. Ir 2980–2930 (CH); 1748 (CO); 1374 (CH$_3$); 1064 (C—O—C); 875–860 cm$^{-1}$. Mass spectrum (10% cutoff) m/e 228, 0.04% (M$^+$); 213, 2.7% (M$^+$ — CH$_3$); 101, 23% (2,2-dimethyl-1,3-dioxacyclopent-4-yl ion); 97, 43%; 57, 100% (CH$_3$CH$_2$C≡O$^+$); 43, 66% (CH$_3$C≡O$^+$). High-resolution MS, calcd for C$_{12}$H$_{21}$O$_3$ (M$^+$ — CH$_3$), 213.1491; found, 213.1490.

Anal. Calcd for C$_{13}$H$_{24}$O$_3$: C, 68.38; H, 10.59. Found: C, 68.17; H, 10.31.

If in place of the racemic iodide 4 there is used (−)-4 there is formed (2'R, 4S)-2'-(2,2-dimethyl-1,3-dioxacyclopent-4-yl)-4'-ξ-methylhept-5'-one, (+)-5; [α]$_D$ +14°.

EXAMPLE 4

(+)-α-(and γ-) Multistriatin (2,4-Dimethyl-5-ethyl-6,8-dioxabicyclo [3.2.1]octane) 1.

To a solution of 150.0 mg (0.66 mmol) of 2'-(2,2-dimethyl-1,3-dioxacyclopent-4-yl)-4'-methylhept-5'-one 5 in 2 ml of CH$_3$CN 1 ml of aqueous 10% HCl was added. The solution was stirred for 18 h at room temperature and then 2 g of NaCl was added to saturation. It was poured into 30 ml of saturated NaCl solution and extracted with 4 × 20 ml of ether. The ether layers were combined and washed with 40 ml of saturated NaHCO$_3$ and dried over MgSO$_4$ and the solvent was removed. This left a clear oil that was distilled in a microstill: 110.2 mg (98%) were collected at bath temperature, 90° C at 20 Torr. This material was shown to be an 85:15 mixture of α:γ-multistriatin by 270-MHz $^1$H NMR and by GLC. The identity of the synthetic material with α-multistriatin was established by the very characteristic NMR, the infrared, and low-resolution mass spectra, all of which were the same as the data published by Silverstein et al. $^1$H NMR δ 4.20, m, 1 H(C-1 H); 3.89, d of d, J=7.0, 0.8 Hz, 1 H(C-7 H); 3.68, d of d, J=7.0, 5.0 Hz, 1 H(C-7 H); 2.06, m, 1 H; 1.83, m, 1 H; 1.73, q, 2 H(CH$_2$CH$_3$); 1.61, m, 1 H; 0.94, t, J=7.0 Hz, 3 H(CH$_2$CH$_3$); 0.81, d, 6 H, J=7 Hz (C-2 and C-4 methyls). Ir 2960–2880 (CH); 1453, 1379, 1361 (CH); 1172, 1124, 1031 (C—O—C); 912, 894 cm$^{-1}$(ring). Mass spectrum (10% cutoff) m/e 170, 3% M$^+$); 128, 11%; 57, 100% (CH$_3$CH$_2$C≡O$^+$). High-resolution MS, calcd for C$_{10}$H$_{18}$O$_2$, 170,1307; found, 170.1307.

If in place of racemic 2'-(2,2-dimethyl-1,3-dioxacyclopent-4-yl)-4'-ξ-methylhept-5'-one 5 there is used (2'R, 4S)-2'-(2,2-dimethyl-1,3-dioxacyclopent-4-yl)-4'-ξ-methylhept-5'-one ((+)-5) there is obtained an 85:15 mixture of (−)-α-multistriatin and (−)-γ-multistriatin: [α]$_D$ −40° (hexane).

EXAMPLE 5

(−)-(5R, 6S)-2,2,5-Trimethyl-6-[(R)-N-α-phenylethylcarbamoyloxy]-1,3-dioxepane ((−)-7).

Into a flame-dried 100-ml flask containing a stirring bar and 60 ml of freshly distilled hexane was added by syringe 5.63 g (35.2 mmol) of (5RS, 6SR)-2,2,5-trimethyl-6-hydroxy-1,3-dioxepane, followed by 4.93 g (33.5 mmol) of (+)-(R)-α-phenethylisocyanate (Norse Laboratories). The flask was fitted with a reflux condenser and flushed with N$_2$. After 4 days at reflux, TLC showed no isocyanate remaining, and the solvent was removed in vacuo. The resulting yellow oil was dissolved in 90 ml of hexane + 15 ml of toluene + 1 ml of pyridine and left in the freezer for 5 days, during which time crystallization occurred. After three recrystallizations from hexane-toluene (9:1 to 5:1), there was obtained 2.32 g (22.5%, 45% of theory) of a solid having mp 103°–103.5° C and [α]$^{23}$D −1.96° (c 1.0, CHCl$_3$). Prior experiments had shown that the rotation of such material does not improve upon further recrystallization. $^1$H NMR δ 7.31, m, 5 H(phenyl H); 5.11, br d, 1 H(NH); 4.82, pentet, J∼6.6 Hz, 1 H (CHN); 4.42, br m, 1 H(CHO); 3.73, two d, J=12, 2 Hz, 2 H(one H each from C-4 and C-7); 3.61, d of d, J=12, 6 Hz, 1 H(C-7 H); 3.40, d of d, J=12, 5.4 Hz, 1 H(C-4 H); 1.86, m, 1 H(CH$_3$CHCH$_2$); 1.49, d, J=7 Hz, 3 H(CH$_3$CHN); 1.33, s, 3 H(CH$_3$CCH$_3$); 1.31, s, 3 H(CH$_3$CCH$_3$); 0.98, d, J=7 Hz, 3 H(CH$_3$CHCH$_2$). $^{13}$C NMR δ 155.3, s(urethane C=O); 143.9, s (quaternary phenyl C); 128.5, d(meta C's); 127.2, d(para C); 125.9, d(ortho C's); 101.1, s(C-2); 76.4, d(C-6); 62.6, t(C-7); 61.3, t(C-4 of dioxepane); 50.9, d(benzyl C); 38.6, d(C-5 of dioxepane); 24.8, q(methyl of C-2); 24.4, q(methyl of C-2); 22.6, q(methyl β to phenyl); 14.4, q(methyl of C-5). Ir 3322 (NH); 1724 (C=O); 1370, 1380 (methyls); 1233, 1214 (acetonide); 846; 704, 763 cm$^{-1}$ (monosubstituted benzene). Mass spectrum (10% cutoff) m/e 308, 0.5% (M$^+$ + 1); 307, 0.05% (M$^+$); 292, 1.8% (M$^+$ − CH$_3$); 250, 10% (M$^+$ − CH$_2$COCH$_3$); 249, 11% (M$^+$ − CH$_3$COCH$_3$); 105, 100% (PhCHCH$_3$$^+$); 84, 26%; 77, 10% (Ph$^+$); 72, 18%; 58, 56% (CH$_3$COCH$_3$$^+$); 43, 36% (CH$_3$C≡O$^+$).

Anal. Calcd for C$_{17}$H$_{25}$NO$_4$: C, 66.42; H, 8.20; N, 4.56. Found: C, 66.50; H, 8.00; N, 4.71.

EXAMPLE 6

(−)-(5R, 6S)-2,2,5-Trimethyl-6-hydroxy-1,3-dioxepane (−)-6.

To 1.06 g (31.1 mmol) of lithium aluminum hydride suspended in 20 ml of THF (freshly distilled from LiAlH$_4$) was added with stirring over a period of 10 min. a solution of 1.96 g (6.4 mmol) of (−)-(5R, 6S)-2,2,5-trimethyl-6-[(R)-N-α-phenethylcarbamoyloxy]-1,3-dioxepane in 10 ml. of THF, while cooling in an ice bath. The mixture was then heated at reflux under N$_2$ for 5 h. The flask was cooled in an ice bath and 2.5 ml of saturated Na$_2$SO$_4$ solution added dropwise with stirring. The resulting white precipitate was filtered and washed with 10 × 6 ml of Et$_2$O. The filtrate was dried over MgSO$_4$ and evaporated, leaving 1.94 g of a mixture of the alcohol and α-phenethylamine. These were separated by a rapid filtration through silica gel. For this purpose the mixture was dissolved in 5 ml of hexane, applied to 15 g of silica gel, and 45 ml of hexane filtered through and discarded. Elution with 20 ml of ether, followed by 30 ml of EtOAc, afforded 1.03 g of the alcohol. Further elution with EtOAc (50 + 100 ml) eluted only amine in small quantities. The alcohol was distilled in a microstill to give 988.3 mg (96%) of pure (−)-6 having [α]$^{23}$D −43.46° (c 1.0, CHCl$_3$). The ir, $^1$H NMR, and mass spectra of this material were identical with those of the racemate.

EXAMPLE 7

(2'R, 4S)-2'-(2,2-Dimethyl-1,3-dioxacyclopent-4-yl)-1'-propanol (−)-2.

(5R, 6S)'2,2,5-Trimethyl-6-hydroxy-1,3-dioxepane (6, 4.00 g, 25 mmol) was placed in a 5-ml flask along with 2 drops (30 μl) of concentrated HCl and a stirring bar. The mixture was distilled through a 10-cm Vigreux column, giving only one fraction, bp 112°–114° C (20 Torr), weighing 3.95 g (98% yield). $^1$H NMR δ 4.12, q, J=6.5 Hz, 1 H(CHO); 4.03, t, J=7.1 Hz, 1 H(CHOCH$_2$O); 3.71, t, J=7.9 Hz, 1 H(CHOCH$_2$O); 3.66, s, 1 H(OH); 3.53, d, J=6.3 Hz, 2 H(CH$_2$OH); 1.85, septet, J=6.5 Hz, 1 H(CH$_3$CH); 1.41, s, 3 H(acetonide CH$_3$); 1.32, s, 3 H(acetonide CH$_3$); 0.96, d, J=7.5 Hz, 3 H(CH$_3$CH). $^{13}$C NMR δ 108.5, s(C-2); 78.0, d(C-4); 67.2, t(C-5); 65.2, t(C-1'); 38.2, d(C-2'); 26.4, q(C-2 methyl cis to alkyl group); 25.3, q(C-2 methyl trans to alkyl group); 12.1, q(C-3'). Ir broad 3600–3200 (OH); 1380, 1370 (methyls); 1212 (acetonide); broad 1060–1040 (C—O); 860 cm$^{-1}$. Mass spectrum (50% cutoff) m/e 145, 69% (M$^+$ − CH$_3$); 101, 62% (2,2-dimethyl-1,3-dioxacyclopent-4-yl ion); 85, 94%; 72, 89%; 59, 51% [CH$_3$C(OH)$^+$ —CH$_3$]; 57, 59%; 55, 59%; 43, 100% (CH$_3$C≡O$^+$); 41, 70%; 31, 50% ($^+$CH$_2$OH). [α]$_D$ −2.7°.

Anal. Calcd for C$_8$H$_{16}$O$_3$: C, 59.98; H, 10.07. Found: C, 60.26; H, 9.79.

The continuation of the synthesis starting with (−)-2 follows the procedures shown in Examples 1 to 4 with the exception that in place of the racemates (±)-2, (±)-3, (±)-4 and (±)-5 there are used (−)-2, (−)-3, (−)-4, and (+)-5.

The invention has been described in detail with particular reference to certain preferred embodiments thereof, but it is understood that variations and modifications can be effected within the spirit and scope of the appended claims.

What is claimed is:

1. A stereocontrolled synthesis of an isomeric mixture containing a major portion of α-multistriatin and a minor portion of γ-multistriatin comprising the steps of:
   (a) forming (2'RS, 4SR')-2'-(2,2-dimethyl-1,3-dioxacyclopent-4-yl)-1'-propyl tosylate by a reaction of the acetonide alcohol having the structure

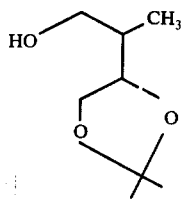

with tosyl chloride;
   (b) forming (2'RS, 4SR)-2'-(2,2-dimethyl-1,3-dioxacyclopent-4-yl)-1'-iodopropane by reaction of the tosylate obtained in step (a) with NaI;
   (c) forming (2'RS, 4SR)-2'-(2,2-dimethyl-1,3-dioxacyclopent-4-yl)-4'-ξ-methylhept-5'-one by preparing the enolate of 3-pentanone with lithium diisopropylamide and alkylating the enolate with the iodopropane obtained in step (b); and
   (d) forming a mixture comprising a major amount of α-multistriatin and a minor amount of γ-multistriatin by removing the acetonide group and cyclizing the ketone obtained in step (c).

2. The synthesis of claim 1 wherein the said tosylate is formed by:
   (a) mixing a pyridine solution containing about 1 part by weight of said acetonide alcohol with about 2 parts by weight of tosyl chloride with stirring at a temperature of about 0° C for about 2 hours and at room temperature for about 3 hours; and
   (b) adding water to the reaction mixture of step (a) and separating therefrom the said tosylate by extraction with ether.

3. The synthesis of claim 2 wherein the said iodopropane is formed by:
   (a) treating about 4 parts by weight of said tosylate in acetone solution with about 5 parts by weight of NaI with stirring for about 18 hours, filtering, and treating the filtrate with an additional 2 parts by weight of NaI with stirring for 30 hours;
   (b) filtering the reaction mixture of step (a) and adding water thereto; and
   (c) isolating the said iodopropane by extraction with ether.

4. The synthesis of claim 3 wherein the said ketone is formed by:
   (a) preparing lithium diisopropylamide by reaction of about 1 equivalent diisopropylamine with about 1 equivalent n-BuLi in tetrahydrofuran solution at about −78° C;
   (b) adding about 1 equivalent of 3-pentanone with stirring for about 0.5 hours while warming the reaction mixture to −40° C;
   (c) adding to the reaction mixture of step (b) about 1 equivalent of said iodopropane and about 2 equivalents of HMPA and stirring at room temperature;
   (d) pouring the reaction mixture of step (c) into saturated NaCl solution and extracting therefrom a crude ketone product with ether;
   (e) removing ether and chromatographing the residual oil on silica gel; and
   (f) isolating said ketone by eluting first unreacted iodopropane then purified ketone from the silica gel.

5. The stereocontrolled synthesis of claim 4 wherein a major portion of α-multistriatin and a minor portion of γ-multistriatin are formed by:
   (a) treating the said ketone in CH₃CN solution with aqueous 10% HCl with stirring at room temperature for about 18 hours;
   (b) pouring the reaction mixture of step (a) into saturated NaCl solution and extracting therefrom a crude mixture of α- and γ-multistriatin with ether; and
   (c) removing ether and distilling the remaining clear oil at about 20 Torr. and a bath temperature of about 90° C to obtain a mixture consisting essentially of a major portion of α-multistriatin and a minor portion of γ-multistriatin.

6. A stereocontrolled synthesis of an isomeric mixture containing a major amount of the (−)-enantiomer of α-multistriatin and a minor amount of the (−)-enantiomer of γ-multistriatin comprising the steps of:
   (a) forming (2R', 4S)-2'-(2,2-dimethyl-1,3-dioxacyclopent-4-yl)-1'-propyl tosylate by reaction of the optically active acetonide alcohol having the formula (2'R, 4S)-2'-(2,2-dimethyl-1,3-dioxacyclopent-4-yl)-1'-propanol with tosyl chloride;
   (b) forming (2'S, 4S)-2'-(2,2-dimethyl-1,3-dioxacyclopent-4-yl)-1'-iodopropane by the reaction of the tosylate obtained in step (a) with NaI;
   (c) forming (2'R, 4S(-2'-(2,2-dimethyl-1,3-dioxacyclopent-4-yl)-4'-ξ-methylhept-5'-one by preparing the enolate of 3-pentanone with lithium diisopropylamide and alkylating the enolate with the iodopropane obtained in step (b); and
   (d) forming a mixture comprising a major amount of the (−)-enantiomer of α-miltistriatin and a minor amount of the (−)-enantiomer of γ-multistriatin by removing the acetonide group and cyclizing the ketone obtained in step (c).

7. The process of claim 6 wherein the optically active acetonide alcohol is prepared by the steps comprising:
   (a) converting the racemate (5RS, 6SR)-2,2,5-trimethyl-6-hydroxy-1,3-dioxepane to two diastereomeric urethane derivatives by reaction with (+)-(R)-α-phenethylisocyanate;
   (b) isolating the (−)-urethane by fractional crystallization;
   (c) reducing the isolated (−)-urethane with lithium aluminum hydride to furnish the optically active (5R, 6S)-2,2,5-trimethyl-6-hydroxy-1,3-dioxepane; and
   (d) converting the (5R, 6S)-2,2,5-trimethyl-6-hydroxy-1,3-dioxepane into the optically active acetonide alcohol (2'R, 4S)-2'-(2,2-dimethyl-1,3-dioxacyclopent-4yl)-1'-propanol by treatment with hydrochloric acid.

* * * * *